United States Patent
Sakamoto et al.

(10) Patent No.: US 6,858,673 B1
(45) Date of Patent: Feb. 22, 2005

(54) COMPOSITION FOR HYDROGEL, HYDROGEL AND USE THEREOF

(75) Inventors: Nobuyuki Sakamoto, Tsukuba (JP); Kenshiro Shuto, Ibaraki (JP); Shujiro Sakaki, Ibaraki (JP); Ken Suzuki, Tsukuba (JP); Shinji Tanaka, Tsukuba (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 10/130,397

(22) PCT Filed: May 9, 2000

(86) PCT No.: PCT/JP00/02953

§ 371 (c)(1),
(2), (4) Date: Jul. 16, 2002

(87) PCT Pub. No.: WO01/34700

PCT Pub. Date: May 17, 2001

(30) Foreign Application Priority Data

Nov. 9, 1999 (JP) .......................... 11/318828

(51) Int. Cl.[7] ....................... C08L 43/02; C08L 101/00; C12N 9/96; A61K 7/00; A61K 9/70
(52) U.S. Cl. ..................... 525/92 R; 525/88; 525/191; 525/209; 525/228; 516/102; 514/944; 514/772.4; 514/772.6
(58) Field of Search ................ 516/102; 514/944; 514/772.4, 772.5, 772.6; 525/57, 191, 209, 88, 92 R, 228, 230

(56) References Cited

U.S. PATENT DOCUMENTS

| | | | | |
|---|---|---|---|---|
| 5,468,475 A | * | 11/1995 | Shaku et al. ............ | 424/70.16 |
| 5,977,257 A | * | 11/1999 | Waki et al. ............ | 525/209 |
| 6,090,901 A | * | 7/2000 | Bowers et al. ............ | 526/277 |
| 6,310,116 B1 | * | 10/2001 | Yasuda et al. ............ | 523/107 |

FOREIGN PATENT DOCUMENTS

| | | | |
|---|---|---|---|
| JP | 03-039309 | 2/1991 | ......... C08F/220/18 |
| JP | 06-157271 A | * 6/1994 | |
| JP | 09-3132 A | * 1/1997 | |

OTHER PUBLICATIONS

Machine translation for JP 06157271 A, http://www6.ipdl.jpo.go.jp/Tokujitu/PAJdetail.ipdl?N0000 =80&N0120=01&N2001=2&N3001=H06–157271, (7 pages), (Sep. 2003).*
Derwent Abstract on EAST, week 200005, London: Derwent Publications Ltd., AN 1994–242962, JP 06157271 A, (Nakabayashi N), abstract.*
JPO on EAST, Patent Abstracts of Japan, JP406157271A (Jun. 1994).*
Machine translation for JP 09003132 A, http://www6.ipdl.jpo.go.jp/Tokujitu/PAJdetail.ipdl?N0000 =80&N0120=01&N2001=2&N3001=H09–003132, (8 pages), (Sep. 2003).*
JPO on EAST, Patent Abstracts of Japan, JP409003132A (Jan. 1997).*

* cited by examiner

*Primary Examiner*—Daniel S. Metzmaier
(74) *Attorney, Agent, or Firm*—Darby & Darby

(57) ABSTRACT

A composition for hydrogels which comprises (A1) a copolymer which comprises 25 to 97 mol % of unit (a) derived from a compound represented by formula (1) and 3 to 75 mol % of unit (b) derived from a monomer represented by formula (2) and is soluble in aqueous media and (B) a polymer which has hydrophilic groups such as hydroxyl or carboxyl groups and is soluble in aqueous media; and a hydrogel comprising the composition. (X represents a divalent organic residue; Y represents alkyleneoxy, etc.; Z, $R^1$, $R^2$, $R^3$, $R^4$, and $L^2$ each represents hydrogen, etc.; and $L^1$ represents —$C_6H_4$—, etc.)

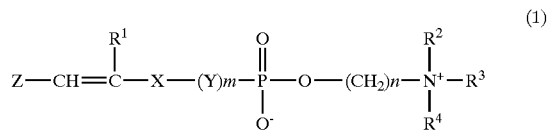

(1)

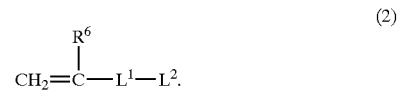

(2)

12 Claims, No Drawings

COMPOSITION FOR HYDROGEL, HYDROGEL AND USE THEREOF

FIELD OF ART

The present invention relates to a hydrogel containing a copolymer including a unit having a phosphorylcholine-like group, which hydrogel has excellent biocompatibility, may be used for various cosmetics, drugs, and the like, and is substantially soluble in water at an ordinary temperature. The present invention also relates to a composition for hydrogel for preparation thereof, a cosmetic material, a dermal plaster, an enzyme stabilizer, and a stabilized enzyme composition, all containing the hydrogel, and to medical equipment and clinical test instrument with a coating of the dried hydrogel.

BACKGROUND ART

It is known that polymers having a phosphorylcholine-like group have excellent biocompatibility such as inactivatability of blood constituents or non-adsorbability of biomaterials, attributed to its phospholipid-like structure originated from biomembrane, and are superior in properties such as antifouling and moisturizing properties. Active research and development have been made for synthesis and use of the polymers having a phosphorylcholine-like group, aiming at development of biomaterials which make good use of such properties, and some investigations have been made of hydrogels containing the polymers having a phosphorylcholine-like group.

For example, it is reported that a hydrogel film has been obtained by dissolving in an ethanol solution a copolymer of a monomer having a hydrophobic functional group and a monomer having a phosphorylcholine-like group, applying the resulting mixture over a substrate, evaporating the ethanol by solvent evaporation to prepare a film, and swelling the film in water (K. Ishihara et al., Japanese Journal of Polymer Science and Technology, 46, P591 (1989)).

With this copolymer for hydrogel films, however, a gel cannot be prepared directly from the copolymer solution, since the preparation of a gel requires formation of a polymer film having a cross-linked structure, followed by swelling in water. The cross-linked hydrogel films thus obtained are substantially insoluble in water at an ordinary temperature.

A method is also reported for preparing a hydrogel that may be used for contact lenses, including mixing and cross-linking a monomer having a phosphorylcholine-like group and a cross-linking monomer (JP-5-107511-A, JP-9-20814-A).

This hydrogel is in the form of a chemically cross-linked clot, and is substantially insoluble in water at an ordinary temperature.

Another method for preparing hydrogel films is also reported, including forming a polyion complex from a polymer having a phosphorylcholine-like group with an anionic functional group and that with a cationic functional group (K. Ishihara et al., J. Biomedical Materials Research, 28., p1347, 1994).

The polyion complex for preparing the hydrogel films cannot substantially be dissolved in water at an ordinary temperature, since each polymer strongly coagulates in an aqueous solution.

DISCLOSURE OF THE INVENTION

It is therefore an object of the present invention to provide a hydrogel which contains a copolymer having a phosphorylcholine-like group, is substantially water-soluble and excellently safe, exhibits favorable properties in various biocompatible materials, cosmetics, and drugs, is capable of enclosing drugs, biopolymers, and biological cells therein, and has no groups that substantially react with such enclosures, and to provide a composition for hydrogel that facilitates preparation of such a hydrogel.

It is another object of the present invention to provide a cosmetic material and a dermal plaster which are substantially soluble in water at an ordinary temperature, are substantially chemically nonreactive to other cosmetic materials or adhesive components for enabling application on skin, have excellent properties such as moisturizing property originating from a compound having a phosphorylcholine-like group, and is excellently safe.

It is yet another object of the present invention to provide medical equipment and a clinical test instrument provided with a coating of dried hydrogel that is excellent in biocompatibility such as inactivatability of blood constituents and non-adsorbability of biomaterials, and is capable of providing antifouling and moisturizing properties.

It is still another object of the present invention to provide an enzyme stabilizer and a stabilized enzyme composition which are capable of stably maintaining enzyme activity for a prolonged period of time.

The present inventors have made intensive researches for solving these problems. With the prior art technique, as mentioned above, a hydrogel containing a copolymer having a phosphorylcholine-like group cannot be prepared without a polymer having a chemically cross-linked structure or having a reactive group of similar function. However, the present inventors have found out that, surprisingly, a hydrogel that is substantially water-soluble at an ordinary temperature may be obtained readily from a particular copolymer having a phosphorylcholine-like group and a particular polymer soluble in an aqueous medium, or from a particular copolymer having a phosphorylcholine-like group and another particular copolymer having a phosphorylcholine-like group. Further, a composition for preparing this hydrogel includes substantially no group that is reactive to pharmaceuticals, biopolymers, or biological cells, so that the composition may be used in preparation of various pharmaceuticals, cosmetics, medical equipment, clinical test instrument, or enzyme stabilizers, to give excellent biocompatibility, moisturizing property, and enzyme stabilizing property attributed to the copolymer having a phosphorylcholine-like group. The inventors found out, in particular, that adjustment of the moisture content of the hydrogel may in turn enable adjustment of dissolution rate of the hydrogel in water, thereby completing the present invention.

According to one aspect of the present invention, there is provided a composition for hydrogel comprising a copolymer (A1) having a phosphorylcholine-like group soluble in an aqueous medium, said copolymer (A1) comprising 25 to 97 mol %

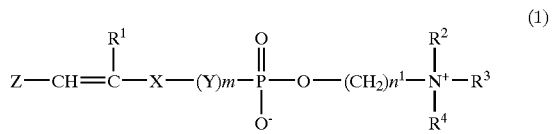

(1)

of unit (a) derived from at least one sort of compounds represented by the formula (1) having a phosphorylcholine-like group, and 3 to 75 mol % of unit (b) derived from at least one sort of hydrophobic monomers represented by the formula (2); and a polymer (B) soluble in an aqueous medium having one or more sorts of hydrophilic groups selected from the group consisting of a hydroxyl group, a carboxyl group, a phosphonic acid group, a sulfonic acid group, an amide group, an amino group, a dialkylamino group, a trialkylammonium salt group, a trialkylphosphonium salt group and a polyoxyethylene group: wherein X represents a divalent organic residue, Y represents an alkyleneoxy group having 1 to 6 carbon atoms, Z represents a hydrogen atom or a group $R^5$—O—CO— (wherein $R^5$ represents an alkyl group having 1 to 10 carbon atoms or a hydroxyalkyl group having 1 to 10 carbon atoms), $R^1$ represents a hydrogen atom or a methyl group, $R^2$, $R^3$ and $R^4$ are the same or different groups and each represents a hydrogen atom or a hydrocarbon or hydroxyhydrocarbon group having 1 to 6 carbon atoms, m is 0 or 1, and $n^1$ is an integer of 2 to 4;

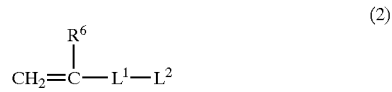

(2)

wherein $L^1$ represents —$C_6H_4$—, —$C_6H_9$—, —(C=O)—O—, —O—, —(C=O)NH—, —O—(C=O)— or —O—(C=O)—O— and $L^2$ represents a hydrophobic functional group selected from a hydrogen atom, —$(CH_2)_{n^2}$—$L^3$ and —$((CH_2)p$-O$)$—$L^3$, wherein $n^2$ is an integer of 1 to 24, p is an integer of 3 to 5 and $L^3$ represents a hydrogen atom, a methyl group, —$C_6H_5$ or —O—$C_6H_5$.

According to another aspect of the present invention, there is provided a composition for hydrogel comprising a copolymer (A2) having a phosphorylcholine-like group soluble in an aqueous medium, said copolymer (A2) comprising 30 to 90 mol % of unit (a) mentioned above, and 10 to 70 mol % of unit (c) derived from a monomer having one or more sorts of hydrophilic groups selected from the group consisting of a hydroxyl group, a carboxyl group, a phosphonic acid group, a sulfonic acid group, an amide group, an amino group, a dialkylamino group, a trialkylammonium salt group, a trialkylphosphonium salt group and a polyoxyethylene group; and a polymer (C) soluble in an aqueous medium having a hydrophobic functional group represented by —$(CH_2)q$-$L^4$ and/or —$((CH_2)r$-O$)q$-$L^4$, wherein $L^4$ represents an hydrogen atom, a methyl group, —$C_6H_5$ or —O—$C_6$Hs, q is an integer of 1 to 24, and r is an integer of 3 to 5.

According to yet another aspect of the present invention, there is provided a composition for hydrogel comprising the above-mentioned copolymer (A1) having a phosphorylcholine-like group soluble in an aqueous medium, and the above-mentioned copolymer (A2) having a phosphorylcholine-like group soluble in an aqueous medium.

According to still another aspect of the present invention, there is provided a hydrogel substantially soluble in water at an ordinary temperature prepared by stirring the above-mentioned composition for hydrogel in an aqueous medium to gelate the composition, and optionally comprising therein one or more of element selected from the group consisting of a drug, a protein, a DNA, an RNA, a biopolymer and a biological cell.

According to another aspect of the present invention, there is provided a cosmetic material, a dermal plaster material, or an enzyme stabilizer, all comprising the above hydrogel.

According to another aspect of the present invention, there is provided medical equipment and a clinical test instrument comprising a coating of the dried hydrogel.

According to yet another aspect of the present invention, there is provided a stabilized enzyme composition comprising the hydrogel and an enzyme.

PREFERRED EMBODIMENT OF THE INVENTION

The hydrogel of the present invention contains a copolymer having a phosphorylcholine-like group, and is substantially soluble in water at an ordinary temperature, i.e. at 20 to 25° C. This hydrogel may be used in preparation of various biocompatible materials, cosmetic materials, pharmaceutical materials, enzyme stabilizers, and the like.

As used herein, "substantially soluble in water at an ordinary temperature" means that the hydrogel does not have a chemically cross-linked structure (a structure established by chemical cross-linking reaction) that renders the hydrogel water-insoluble at an ordinary temperature, and when immersed in water at an ordinary temperature, the hydrogel dissolves in about 8 to 96 hours, depending on its moisture content and its constitutional polymers. Here, "dissolve" means that the hydrogel elutes into the medium to form a homogeneous liquid.

The composition for hydrogel for preparation thereof according to the present invention is made up of any of the following three combinations (i) to (iii):
(i) a composition containing a particular copolymer (A1) having a phosphorylcholine-like group and a particular polymer (B);
(ii) a composition containing a particular copolymer (A2) having a phosphorylcholine-like group and a particular polymer (C); or
(iii) a composition containing a particular copolymer (A1) having a phosphorylcholine-like group and a particular copolymer (A2) having a phosphorylcholine-like group.

The particular copolymer (A1) having a phosphorylcholine-like group is soluble in an aqueous medium and includes 25 to 97 mol % of unit (a) derived from at least one sort of compounds represented by the formula (1) having a phosphorylcholine-like group, and 3 to 75 mol % of unit (b) derived from at least one sort of hydrophobic monomers represented by the formula (2).

Copolymer (A1) may be composed of units (a) and (b), or may optionally contain other compositional units. In other words, the sum of units (a) and (b) does not have to be 100 mol %. The kinds of such other compositional units, when contained, are not particularly limited as long as the resulting copolymer (A1) is soluble in an aqueous medium. The content of such other units is preferably not more than 70 mol %, more preferably not more than 50 mol %.

"Soluble in an aqueous medium" means that liquid having high fluidity results when copolymer (A1) is dissolved at 5 wt % concentration in a liquid prepared by mixing water and a hydrophilic organic medium such as methanol, ethanol, 1-propanol, 2-propanol, N,N-dimethylformamide, N,N-dimethylacetamide, dimethylsulfoxide, glycerine, acetonitrile, acetone, or mixtures thereof; or in an aqueous medium such as an aqueous solution of one or more salts selected from sodium chloride, potassium chloride, phosphate, or borate; or preferably in water at an ordinary temperature. In the following discussion regarding other components, "soluble in an aqueous medium" means the same.

The molecular weight of copolymer (A1) is not particularly limited as long as the copolymer is soluble in an aqueous medium, and is usually in the range of 10000 to 5000000 in weight average molecular weight.

Examples of the compound represented by the formula (1) having a phosphorylcholine-like group for unit (a) may include 2-(meth)acryloyloxyethyl-2'-(trimethylammonio) ethyl phosphate, 3-(meth)acryloyloxypropyl-2'-(trimethylammonio)ethyl phosphate, 4-(meth) acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth) acryloyloxyethyl-21-(triethylammonio)ethyl phosphate, 2-(meth)acryloyloxyethyl-2'-(tripropylammonio)ethyl phosphate, 2-(meth)acryloyloxyethyl-2'-(tributylammonio) ethyl phosphate, 2-(meth)acryloyloxypropyl-2'-(trimethylammonio)ethyl phosphate, 2-(meth) acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(vinyloxy) ethyl-2-(trimethylammonio) ethyl phosphate, 2-(allyloxy)ethyl-2-(trimethylammonio)ethyl phosphate, 2-(p-vinylbenzyloxy) ethyl-2'-(trimethylammonio)ethyl phosphate, 2-(p-vinylbenzoyloxy)ethyl-2'-(trimethylammonio)ethyl phosphate, 2-(styryloxy)ethyl-2'-(trimethylammonio)ethyl phosphate, 2-(p-vinylbenzyl)ethyl-2'-(trimethylammonio) ethyl phosphate, 2-(vinyloxycarbonyl)ethyl-2'-(trimethylammonio)ethyl phosphate, 2-(allyloxycarbonyl) ethyl-2'-(trimethylammonio)ethyl phosphate, 2-(acryloylamino)ethyl-2'-(trimethylammonio)ethyl phosphate, 2-(vinylcarbonylamino)ethyl-2'-(trimethylammonio)ethyl phosphate, 2-(allyloxycarbonylamino)ethyl-2'-(trimethylammonio) ethyl phosphate, 2-(butenoyloxy)ethyl-2'-(trimethylammonio)ethyl phosphate, 2-(crotonoyloxy)ethyl-2'-(trimethylammonio)ethyl phosphate, ethyl-(2'-trimethylammonioethylphosphorylethyl) fumarate, butyl-(2'-trimethylammonioethylphosphorylethyl) fumarate, hydroxyethyl-(2'-trimethylammonioethylphosphorylethyl) fumarate, ethyl-(2'-trimethylammonioethylphosphorylethyl) fumarate, butyl-(2'-trimethylammonioethylphosphorylethyl) fumarate, and hydroxyethyl-(2'-trimethylammonioethylphosphorylethyl) fumarate. Among these, 2-methacryloyloxyethyl-2'-(trimethylammonio)ethyl phosphate (abbreviated as MPC hereinbelow) is particularly preferable for its availability and biocompatibility. These compounds may be used solely or as a mixture.

The compound having a phosphorylcholine-like group may be prepared by a publicly known method as disclosed, for example, in JP-S54-63025-A or JP-S58-154591-A.

The hydrophobic monomer represented by the formula (2) for unit (b) may be, for example, methyl (meth)acrylate, ethyl (meth)acrylate, butyl (meth)acrylate, 2-ethylhexyl (meth)acrylate, lauryl (meth)acrylate, stearyl (meth) acrylate, benzyl (meth)acrylate, phenoxyethyl (meth) acrylate, cyclohexyl (meth)acrylate, polypropylene glycol (meth)acrylate, styrene, methylstyrene, chloromethylstyrene, methyl vinyl ether, butyl vinyl ether, vinyl acetate, or vinyl propionate.

Examples of a preferred combination of the compound having a phosphorylcholine-like group for unit (a) and the hydrophobic monomer for unit (b) in copolymer (A1) may include 2-(meth)acryloyloxyethyl-2'-(trimethylammonio) ethyl phosphate-methyl methacrylate, 2-(meth) acryloyloxyethyl-2'-(trimethylammonio)ethyl phosphate-ethyl (meth)acrylate, 2-(meth)acryloyloxyethyl-2'-(trimethylammonio)ethyl phosphate-butyl (meth)acrylate, 2-(meth)acryloyloxyethyl-2'-(trimethylammonio)ethyl phosphate-2-ethylhexyl (meth)acrylate, 2-(meth) acryloyloxyethyl-2'-(trimethylammonio)ethyl phosphate-lauryl (meth)acrylate, 2-(meth)acryloyloxyethyl-2'-(trimethylammonio)ethyl phosphate-stearyl (meth)acrylate, 2-(meth)acryloyloxyethyl-2'-(trimethylammonio)ethyl phosphate-benzyl (meth)acrylate, and 2-(meth) acryloyloxyethyl-2'-(trimethylammonio)ethyl phosphate-styrene.

As mentioned above, copolymer (A1) may optionally contain other constitutional units, which may be a compound such as vinyl pyrrolidone, acrylonitrile, or glycosyloxyethyl methacrylate. Copolymers (A1) containing such units combined with preferable units (a) and (b) may also preferably be used.

Copolymer (A1) may be prepared, for example, through an ordinary radical copolymerization.

The compound having a phosphorylcholine-like group for unit (a) and the hydrophobic monomer for unit (b) may be provided at such a ratio that the ratio of units (a) and (b) mentioned above is achieved. For example, when the content of unit (b) is less than 3 mol %, a hydrogel cannot be formed sufficiently, whereas when more than 75 mol %, the resulting copolymer (A1) will become hard to be dissolved in an aqueous medium. On the other hand, when the content of unit (a) is less than 25 mol %, sufficient biocompatibility will not be given to the resulting hydrogel, whereas when more than 97 mol %, a hydrogel will be hard to be formed.

The particular polymer (B) is soluble in an aqueous medium, and has one or more sorts of hydrophilic groups selected from the group consisting of a hydroxyl group, a carboxyl group, a phosphonic acid group, a sulfonic acid group, an amide group, an amino group, a dialkylamino group, a trialkylammonium salt group, a trialkylphosphonium salt group and a polyoxyethylene group. The content of the hydrophilic groups is not particularly limited as long as polymer (B) is soluble in an aqueous medium, and may suitably be decided.

Examples of polymer (B) may include polyvinyl alcohol, polyacrylic acid, poly(methacryloyloxyphosphonic acid), polyacrylamide, polyallylamine hydrochloride, poly (dimethylaminoethyl methacrylate), polyethylene glycol, acrylic acid-acrylamide copolymer, acrylic acid-polyethylene glycol monomethacrylate copolymer, polystyrenesulfonic acid, polyglycerin, maleic acid copolymer, guar gum, arabic gum, xanthan gum, gellan gum, hyaluronic acid, collagen, gelatin, casein, methyl cellulose, hydroxyethyl cellulose, carboxymethyl cellulose, alginic acid, and carboxymethyl starch.

The molecular weight of polymer (B) is not particularly limited as long as the polymer is soluble in an aqueous medium, and is usually in the range of about 10000 to about 5000000 in weight average molecular weight.

The particular copolymer (A2) having a phosphorylcholine-like group is soluble in an aqueous medium and includes 30 to 90 mol % of unit (a) mentioned above and 10 to 70 mol % of unit (c) derived from a monomer having one or more sorts of hydrophilic groups selected from the group consisting of a hydroxyl group, a carboxyl group, a phosphonic acid group, a sulfonic acid group, an amide group, an amino group, a dialkylamino group, a trialkylammonium salt group, a trialkylphosphonium salt group and a polyoxyethylene group.

Copolymer (A2) may be composed of units (a) and (c), or may optionally contain other compositional units. In other words, the sum of units (a) and (c) does not have to be 100 mol %. The kinds of such other compositional units, when contained, are not particularly limited as long as the resulting copolymer (A2) is soluble in an aqueous medium. The content of such other units is preferably not more than 70 mol %, more preferably not more than 50 mol %.

The molecular weight of copolymer (A2) is not particularly limited, as long as the copolymer is soluble in an aqueous medium, and is usually in the range of 10000 to 5000000 in weight average molecular weight. Unit (a) mentioned above is the same as that in copolymer (A1).

Examples of the monomer for unit (c) having one or more sorts of hydrophilic groups selected from the group consisting of a hydroxyl group, a carboxyl group, a phosphonic acid group, a sulfonic acid group, an amide group, an amino group, a dialkylamino group, a trialkylammonium salt group, a trialkylphosphonium salt group and a polyoxyethylene group, may include 2-hydroxyethyl (meth)acrylate, 4-hydroxybutyl (meth)acrylate, (meth)acrylic acid, styrenesulfonic acid, (meth)acrylamide, (meth)acryloyloxy phosphonic acid, aminoethyl methacrylate, dimethylaminoethyl (meth)acrylate, and polyethylene glycol (meth)acrylate.

Examples of a preferred combination of the compound having a phosphorylcholine-like group for unit (a) and the monomer having one or more sorts of hydrophilic groups for unit (c) in copolymer (A2) may include
2-(meth)acryloyloxyethyl-2'-(trimethylammonio)ethyl phosphate-2-hydroxyethyl methacrylate,
2-(meth)acryloyloxyethyl-2'-(trimethylammonio)ethyl phosphate-(meth)acrylic acid,
2-(meth)acryloyloxyethyl-2'-(trimethylammonio)ethyl phosphate-styrenesulfonic acid,
2-(meth)acryloyloxyethyl-2'-(trimethylammonio)ethyl phosphate-(meth)acrylamide,
2-(meth)acryloyloxyethyl-2'-(trimethylammonio)ethyl phosphate-aminoethyl (meth)acrylate,
2-(meth)acryloyloxyethyl-2'-(trimethylammonio)ethyl phosphate-dimethylaminoethyl (meth)acrylate, and
2-(meth)acryloyloxyethyl-2'-(trimethylammonio)ethyl phosphate-polyethylene glycol mono(meth)acrylate.

Copolymer (A2) may be prepared, for example, through an ordinary radical copolymerization.

The compound having a phosphorylcholine-like group for unit (a) and the monomer having one or more sorts of hydrophilic groups for unit (c) may be provided at such a ratio that the ratio of units (a) and (c) mentioned above is achieved. For example, when the content of unit (a) is less than 30 mol %, sufficient biocompatibility will not be given, whereas when more than 90 mol %, a hydrogel will be hard to be formed. On the other hand, when the content of unit (c) is less than 10 mol %, a hydrogel will not be formed sufficiently, whereas when more than 70 mol %, sufficient biocompatibility will not be given.

The particular polymer (C) mentioned above is soluble in an aqueous medium and has a hydrophobic functional group represented by —(CH$_2$)q-L$^4$ and/or —((CH$_2$)$_r$—O)q-L$^4$, wherein L$^4$ represents a hydrogen atom, a methyl group, —C$_6$H$_5$ or —O—C$_6$H$_5$, q is an integer of 1 to 24, and r is an integer of 3 to 5.

The molecular weight of polymer (C) is not particularly limited as long as the polymer is soluble in an aqueous medium, and is usually in the range of about 10000 to about 5000000 in weight average molecular weight.

Examples of the hydrophobic functional group, which is an indispensable part of polymer (C), may include an alkyl group such as a methyl, ethyl, propyl, butyl, ethylhexyl, lauryl, or stearyl group; an aromatic functional group such as a phenyl, benzyl, or phenoxy group; or an alkyleneoxy group such as a polypropyleneoxy or polytetramethyleneoxy group.

Examples of polymer (C) having such a hydrophobic functional group may include acrylic acid-acrylamide-ethyl acrylate copolymer, acrylic acid-butyl methacrylate copolymer, methacrylic acid-stearyl methacrylate copolymer, ethylene oxide-propylene oxide block copolymer, vinyl pyrrolidone-styrene copolymer, and propyl cellulose.

Examples of a preferred combination of copolymer (A1) and polymer (B) in composition (i) above may include 2-(meth)acryloyloxyethyl-2'-(trimethylammonio)ethyl phosphate-butyl (meth)acrylate copolymer and (meth)acrylic acid homopolymer; 2-(meth)acryloyloxyethyl-2'-(trimethylammonio)ethyl phosphate-butyl(meth)acrylate copolymer and (meth)acrylic acid-methyl (meth)acrylate copolymer; 2-(meth)acryloyloxyethyl-21-(trimethylammonio)ethyl phosphate-butyl (meth)acrylate copolymer and (meth)acrylic acid-ethyl(meth)acrylate copolymer; 2-(meth)acryloyloxyethyl-2'-(trimethylammonio)ethyl phosphate-butyl (meth)acrylate copolymer and (meth)acrylic acid-n-butyl (meth)acrylate copolymer; 2-(meth)acryloyloxyethyl-2'-(trimethylammonio)ethyl phosphate-butyl(meth)acrylate copolymer and (meth)acrylic acid-2-ethylhexyl (meth)acrylate copolymer; 2-(meth)acryloyloxyethyl-2'-(trimethylammonio)ethyl phosphate-butyl methacrylate copolymer and (meth)acrylic acid-lauryl (meth)acrylate copolymer; 2-(meth)acryloyloxyethyl-2'-(trimethylammonio) ethyl phosphate-butyl (meth) acrylate copolymer and (meth)acrylic acid-stearyl (meth)acrylate copolymer; 2-(meth)acryloyloxyethyl-2'-(trimethylammonio) ethyl phosphate-butyl (meth)acrylate copolymer and (meth)acrylic acid-benzyl (meth)acrylate copolymer; 2-(meth)acryloyloxyethyl-2'-(trimethylammonio) ethyl phosphate-butyl (meth)acrylate copolymer and (meth)acrylic acid-styrene copolymer; 2-(meth)acryloyloxyethyl-2'-(trimethylammonio)ethyl phosphate-2-ethylhexyl (meth)acrylate copolymer and (meth)acrylic acid homopolymer; 2-(meth)acryloyloxyethyl-21-(trimethylammonio)ethyl phosphate-2-ethylhexyl (meth)acrylate copolymer and (meth)acrylic acid-methyl (meth)acrylate copolymer; 2-(meth)acryloyloxyethyl-21-(trimethylammonio)ethyl phosphate-2-ethylhexyl (meth)acrylate copolymer and (meth)acrylic acid-ethyl (meth)acrylate copolymer; 2-(meth)acryloyloxyethyl-21-(trimethylammonio)ethyl phosphate-2-ethylhexyl (meth)acrylate copolymer and (meth)acrylic acid-n-butyl(meth)acrylate copolymer; 2-(meth)acryloyloxyethyl-21-(trimethylammonio)ethyl phosphate-2-ethylhexyl (meth)acrylate copolymer and (meth)acrylic acid-2-ethylhexyl (meth)acrylate copolymer; 2-(meth)acryloyloxyethyl-21-(trimethylammonio)ethyl phosphate-2-ethylhexyl (meth)acrylate copolymer and (meth) acrylic acid-lauryl (meth)acrylate copolymer; 2-(meth)acryloyloxyethyl-2'-(trimethylammonio)ethyl phosphate-2-ethylhexyl (meth)acrylate copolymer and (meth) acrylic acid-stearyl (meth)acrylate copolymer; 2-(meth)acryloyloxyethyl-2'-(trimethylammonio)ethyl phosphate-2-ethylhexyl (meth)acrylate copolymer and (meth)acrylic acid-benzyl (meth)acrylate copolymer; 2-(meth)acryloyloxyethyl-2'-(trimethylammonio)ethyl phosphate-2-ethylhexyl (meth)acrylate copolymer and (meth) acrylic acid-styrene copolymer; 2-(meth)acryloyloxyethyl-2'-(trimethylammonio)ethyl phosphate-lauryl (meth)acrylate copolymer and (meth)acrylic acid homopolymer; 2-(meth)acryloyloxyethyl-2'-(trimethylammonio)ethyl phosphate-lauryl (meth)acrylate copolymer and (meth)acrylic acid-methyl (meth)acrylate copolymer; 2-(meth)acryloyloxyethyl-2'-(trimethylammonio)ethyl phosphate-lauryl (meth)acrylate copolymer and (meth)acrylic acid-ethyl (meth)acrylate copolymer; 2-(meth)acryloyloxyethyl- 2'-(trimethylammonio)ethyl phosphate-lauryl (meth) acrylate copolymer and (meth) acrylic acid-n-butyl (meth) acrylate copolymer; 2-(meth)acryloyloxyethyl-2'-(trimethylammonio)ethyl phosphate-lauryl (meth)acrylate copolymer and (meth)acrylic acid-2-ethylhexyl (meth) acrylate copolymer; 2-(meth)acryloyloxyethyl-2'-(trimethylammonio)ethyl phosphate-lauryl (meth)acrylate copolymer and (meth)acrylic acid-lauryl (meth)acrylate copolymer; 2-(meth)acryloyloxyethyl-2'-(trimethylammonio)ethyl phosphate-lauryl (meth)acrylate copolymer and (meth)acrylic acid-stearyl (meth)acrylate copolymer; 2-(meth)acryloyloxyethyl-2'-(trimethylammonio)ethyl phosphate-lauryl (meth)acrylate copolymer and (meth)acrylic acid-benzyl (meth)acrylate copolymer; 2-(meth)acryloyloxyethyl-2'-(trimethylammonio)ethyl phosphate-lauryl (meth)acrylate copolymer and (meth)acrylic acid-styrene copolymer; 2-(meth)acryloyloxyethyl-2'-(trimethylammonio)ethyl phosphate-stearyl (meth)acrylate copolymer and (meth) acrylic acid homopolymer; 2-(meth)acryloyloxyethyl-2'-(trimethylammonio)ethyl phosphate-stearyl (meth)acrylate copolymer and (meth)acrylic acid-methyl (meth)acrylate copolymer; 2-(meth)acryloyloxyethyl-2'-(trimethylammonio)ethyl phosphate-stearyl (meth)acrylate copolymer and (meth)acrylic acid-ethyl (meth)acrylate copolymer; 2-(meth)acryloyloxyethyl-2'-(trimethylammonio)ethyl phosphate-stearyl (meth)acrylate copolymer and (meth)acrylic acid-n-butyl (meth)acrylate copolymer; 2-(meth)acryloyloxyethyl-2'-(trimethylammonio)ethyl phosphate-stearyl (meth)acrylate copolymer and (meth)acrylic acid-2-ethylhexyl (meth) acrylate copolymer; 2-(meth)acryloyloxyethyl-2'-(trimethylammonio)ethyl phosphate-stearyl (meth)acrylate copolymer and (meth)acrylic acid-lauryl (meth)acrylate copolymer; 2-(meth)acryloyloxyethyl-2'-(trimethylammonio)ethyl phosphate-stearyl (meth) acrylate copolymer and (meth) acrylic acid-stearyl (meth)acrylate copolymer; 2-(meth)acryloyloxyethyl-2'-(trimethylammonio)ethyl phosphate-stearyl (meth)acrylate copolymer and (meth)acrylic acid-benzyl (meth)acrylate copolymer; 2-(meth)acryloyloxyethyl-2'-(trimethylammonio)ethyl phosphate-stearyl (meth)acrylate copolymer and (meth) acrylic acid-styrene copolymer; 2-(meth)acryloyloxyethyl-2'-(trimethylammonio)ethyl phosphate-benzyl (meth)acrylate copolymer and (meth) acrylic acid homopolymer; 2-(meth)acryloyloxyethyl-2'-(trimethylammonio)ethyl phosphate-benzyl (meth)acrylate copolymer and (meth)acrylic acid-methyl (meth)acrylate copolymer; 2-(meth)acryloyloxyethyl-2'-(trimethylammonio)ethyl phosphate-benzyl (meth)acrylate copolymer and (meth)acrylic acid-ethyl (meth)acrylate copolymer; 2-(meth)acryloyloxyethyl-2'-(trimethylammonio)ethyl phosphate-benzyl (meth)acrylate copolymer and (meth) acrylic acid-n-butyl (meth)acrylate copolymer; 2-(meth)acryloyloxyethyl-2'-(trimethylammonio)ethyl phosphate-benzyl (meth)acrylate copolymer and (meth)acrylic acid-2-ethylhexyl (meth) acrylate copolymer; 2 (meth)acryloyloxyethyl-2'-(trimethylammonio)ethyl phosphate-benzyl (meth)acrylate copolymer and (meth)acrylic acid-lauryl (meth)acrylate copolymer; 2-(meth)acryloyloxyethyl-2'-(trimethylammonio)ethyl phosphate-benzyl (meth)acrylate copolymer and (meth)acrylic acid-stearyl (meth)acrylate copolymer; 2-(meth)acryloyloxyethyl-2'-(trimethylammonio)ethyl phosphate-benzyl (meth)acrylate copolymer and (meth)acrylic acid-benzyl (meth)acrylate copolymer; 2-(meth)acryloyloxyethyl-2'-(trimethylammonio)ethyl phosphate-benzyl (meth)acrylate copolymer and (meth)acrylic acid-styrene copolymer; 2-(meth)acryloyloxyethyl-2'-(trimethylammonio)ethyl phosphate-styrene copolymer and (meth)acrylic acid homopolymer; 2-(meth)acryloyloxyethyl-2'-(trimethylammonio)ethyl phosphate-styrene copolymer and (meth)acrylic acid-n-butyl (meth)acrylate copolymer; 2-(meth)acryloyloxyethyl-2'-(trimethylammonio)ethyl phosphate-styrene copolymer and (meth)acrylic acid-2-ethylhexyl (meth)acrylate copolymer; 2-(meth)acryloyloxyethyl-2'-(trimethylammonio)ethyl phosphate-styrene copolymer and (meth)acrylic acid-lauryl (meth)acrylate copolymer; 2-(meth)acryloyloxyethyl-2'-(trimethylammonio)ethyl phosphate-styrene copolymer and (meth)acrylic acid-stearyl (meth)acrylate copolymer; 2-(meth)acryloyloxyethyl-2'-(trimethylammonio)ethyl phosphate-styrene copolymer and (meth)acrylic acid-benzyl (meth)acrylate copolymer; and 2-(meth)acryloyloxyethyl-2'-(trimethylammonio)ethyl phosphate-styrene copolymer and (meth)acrylic acid-styrene copolymer.

In composition (i), the ratio of copolymer (A1) to polymer (B) is not particularly limited as long as a hydrogel is formed in accordance with the method to be discussed later, and is preferably 1:15 to 15:1, more preferably 5:1 to 1:5 in weight ratio.

Each of copolymer (A1) and polymer (B) may either be in a solid form such as powders, or in the form of a solution wherein each solute is dissolved in an aqueous medium, in particular, water. The concentration of the solution is not particularly limited as long as the solute is dissolved. However, when the concentration of the solute in the aqueous medium is extremely low, a hydrogel may not be formed, so that the concentration is preferably about 0.5 to 70 wt %.

Composition (i) may optionally contain, in addition to copolymer (A1) and polymer (B), other components that will not disturb formation of a hydrogel, depending on the use of the resulting hydrogel.

Examples of a preferred combination of copolymer (A2) and polymer (C) in composition (ii) above may include 2-(meth)acryloyloxyethyl-2'-(trimethylammonio)ethyl phosphate-(meth) acrylic acid copolymer and acrylic acid-acrylamide-ethyl acrylate copolymer; 2-(meth) acryloyloxyethyl-2'-(trimethylammonio)ethyl phosphate-(meth) acrylic acid copolymer and acrylic acid-butyl methacrylate copolymer; 2-(meth)acryloyloxyethyl-2'-(trimethylammonio)ethyl phosphate-(meth)acrylic acid copolymer and acrylic acid-stearyl methacrylate copolymer; 2-(meth)acryloyloxyethyl-21-(trimethylammonio)ethyl phosphate-(meth)acrylic acid copolymer and ethylene oxide-propylene oxide block copolymer; 2-(meth) acryloyloxyethyl-2'-(trimethylammonio)ethyl phosphate-(meth)acrylic acid copolymer and vinyl pyrrolidone-styrene copolymer; and 2-(meth)acryloyloxyethyl-2'-(trimethylammonio)ethyl phosphate-(meth)acrylic acid copolymer and acrylic acid-propyl cellulose.

In composition (ii), the ratio of copolymer (A2) to polymer (C) is not particularly limited as long as a hydrogel is formed in accordance with the method to be discussed later, and is preferably 1:15 to 15:1, more preferably 5:1 to 1:5 in weight ratio.

Each of copolymer (A2) and polymer (C) may either be in a solid form such as powders, or in the form of a solution wherein each solute is dissolved in an aqueous medium, in particular, water. The concentration of the solution is not particularly limited as long as the solute is dissolved.

However, when the concentration of the solute in the aqueous medium is extremely low, a hydrogel may not be formed, so that the concentration is preferably about 0.5 to 70 wt %.

Composition (ii) may optionally contain, in addition to copolymer (A2) and polymer (C), other components that will not disturb formation of a hydrogel, depending on the use of the resulting hydrogel.

Examples of a preferred combination of copolymer (A1) and copolymer (A2) in composition (iii) above may include 2-(meth)acryloyloxyethyl-2'-(trimethylammonio)ethyl phosphate-butyl (meth)acrylate copolymer and 2-(meth)acryloyloxyethyl-2'-(trimethylammonio)ethyl phosphate-(meth)acrylic acid copolymer; 2-(meth)acryloyloxyethyl-21-(trimethylammonio)ethyl phosphate-2-ethylhexyl (meth)acrylate copolymer and 2-(meth)acryloyloxyethyl-2'-(trimethylammonio)ethyl phosphate-(meth)acrylic acid copolymer; 2-(meth)acryloyloxyethyl-21-(trimethylammonio)ethyl phosphate-lauryl (meth)acrylate copolymer and 2-(meth)acryloyloxyethyl-2'-(trimethylammonio)ethyl phosphate-(meth)acrylic acid copolymer; and 2-(meth)acryloyloxyethyl-2'-(trimethylammonio)ethyl phosphate-stearyl (meth)acrylate copolymer and 2-(meth)acryloyloxyethyl-2'-(trimethylammonio)ethyl phosphate-(meth)acrylic acid copolymer.

In composition (iii), the ratio of copolymer (A1) to copolymer (A2) is not particularly limited as long as a hydrogel is formed in accordance with the method to be discussed later, and is preferably 1:15 to 15:1, more preferably 5:1 to 1:5 in weight ratio.

Each of copolymer (A1) and copolymer (A2) may either be in a solid form such as powders, or in the form of a solution wherein each solute is dissolved in an aqueous medium, in particular, water. The concentration of the solution is not particularly limited as long as the solute is dissolved. However, when the concentration of the solute in the aqueous medium is extremely low, a hydrogel may not be formed, so that the concentration is preferably about 0.5 to 70 wt %.

Composition (iii) may optionally contain, in addition to copolymer (A1) and copolymer (A2), other components that will not disturb formation of a hydrogel, depending on the use of the resulting hydrogel.

The hydrogel of the present invention is prepared by stirring or mixing any one of the compositions (i) to (iii) for hydrogel in an aqueous medium to gelate the same, and is substantially soluble in water at an ordinary temperature. Further, the present hydrogel may be liquefied into its solution state, preferably by heating to 90° C. or higher or by redissolution in an aqueous medium, and may be regelated by cooling.

The strength of the present hydrogel may be adjusted, for example, by alternately repeating drying of the hydrogel to reduce its moisture content or to completely dry the hydrogel, and swelling in an aqueous medium.

The moisture content of the hydrogel of the present invention is not particularly limited, and may suitably be selected according to its use. Usually, the moisture content of the hydrogel is 0.5 to 70 wt %.

The gelation by stirring in an aqueous medium may be effected, for example in which composition (i) is employed, by process (1) of separately dissolving a suitable amount of each of the essential components; copolymer (A1) and polymer (B), in an aqueous medium mentioned above, and mixing the resulting aqueous solutions together at an ordinary temperature to effect gelation; by process (2) of mixing copolymer (A1) and polymer (B) in solid forms such as powders, and mixing an aqueous medium mentioned above with the resulting solid mixture at an ordinary temperature to effect gelation; or by process (3) of separately dissolving copolymer (A1) and polymer (B) in separate aqueous media mentioned above at higher dilution ratios, such that a mixture of the resulting solutions will be kept in a fluid state and not form a gel, and concentrating the resulting mixture to effect gelation.

In the above process (1) wherein a hydrogel is directly obtained by mixing the solutions, each of the solutions may preferably be prepared by dissolving in an aqueous medium each component at an appropriate concentration of 0.5 to 75 wt % at an ordinary temperature, which leads to ready preparation of a homogeneous hydrogel.

The hydrogel of the present invention may enclose components which are nonreactive to the hydrogel. Examples of such nonreactive components may include drugs such as disinfectants, antimicrobial agents, antiviral agents, hemostatics, antiphlogistics, anesthetics, analgesics, or nutritional supplements; biopolymers such as peptides, plasma derivative proteins, enzymes, or nucleus-related materials; various biological cells; or mixtures thereof. In other words, components nonreactive to the hydrogel may be combined with the composition for hydrogel to provide stabilization or protection of these components. Such combined composition may be prepared, for example, by dissolving or suspending the nonreactive components in the aqueous medium to be used for gelation before effecting the gelation.

The hydrogel of the present invention, being substantially soluble in water at an ordinary temperature, may be used as a storage stabilizer for the above drugs, biopolymers, and biological cells, a carrier for in vivo delivery system, and a capsule material for insertion into the body.

The mixing ratio of these nonreactive components may suitably be decided depending on their object and use.

There is no particular limitation imposed on the cosmetic material and the dermal plaster of the present invention as long as they contain the hydrogel or the hydrogel enclosing the various components mentioned above. The cosmetic material and the dermal plaster may also contain materials that are usually employed in cosmetics or dermal plasters, depending on their kind and object. The cosmetic materials may be in the form of, for example, cleansing foam, lotion, emulsion, cream, gel, essence, face masks, and face packs, but not limited to these.

The hydrogel of the present invention exhibits a stabilizing effect, when added to the water phase of the emulsion type cosmetics such as cream and essence, to stably keep various emulsion states such as W/O, W/O/W, and O/W. The present hydrogel maybe added to the emulsion type cosmetics, for example, by first forming the hydrogel of the present invention, and then emulsifying in a homogenizer, or by separately adding each of the polymers constituting the hydrogel, and forming the hydrogel during the emulsifying process.

The mixing ratio, moisture content, and form of the hydrogel to be contained in the cosmetic materials or the dermal plasters may suitably be selected depending on their kinds and objects.

The medical equipment and clinical test instrument according to the present invention are provided with a coating of dried hydrogel prepared from the hydrogel or the hydrogel enclosing various components mentioned above.

The coating of dried hydrogel may be prepared, for example, by heating the hydrogel or redissolving the hydrogel in an aqueous medium to liquefy the gel into a solution form, and forming the solution into a film followed by drying.

The conditions for heating to liquefy the hydrogel into a solution form may suitably be selected, depending on the kind of the hydrogel, but usually the hydrogel may be made into a solution form by heating to 90° C. or higher.

The solution may be formed into a film and cooled to obtain a hydrogel film, which may then be dried through an ordinary drying process. For example, in order to maintain the nature of each polymer component in the hydrogel, the drying is preferably effected at 60 to 150° C.

The moisture content of the coating of dried hydrogel is usually 0 to 95%. The thickness of the coating is not particularly limited, and may usually be in the range of 0.1 μm to 5 mm. The dissolution rate of the dried hydrogel coating in water at an ordinary temperature is extremely slower than that of the hydrogel, but the coating essentially dissolves in water at an ordinary temperature even though it takes time.

By forming the coating of dried hydrogel on desired surfaces, the medical equipment and clinical test instrument of the present invention may be provided with various properties of the hydrogel, for example, biocompatibility such as inactivatability of blood constituents and non-adsorbability of biomaterials, as well as antifoulting and moisturizing properties.

Examples of the medical equipment which requires such properties may include hemodialysis membranes, intracatheters, guide wires, subcutaneous sensors, and transfusion bags. Examples of the clinical test instrument which requires such properties may include test tubes, vacuum syringes, protein storage vessels, and plates for clinical testing.

The enzyme stabilizer of the present invention contains the above hydrogel. The present enzyme stabilizer may coexist with an enzyme in a stabilized enzyme composition to be discussed below, and may stably maintain the enzyme activity for a prolonged period of time.

The stabilized enzyme composition of the present invention contains the hydrogel and an enzyme.

There is no particular limitation imposed on the enzyme, and various enzymes may be used which is conveniently used when stabilized. Specific examples of such enzyme may include oxidoreductase, transferase, hydrolase, lyase, isomerase, and synthetase. Examples of the oxidoreductase may include glucose oxidase, cholesterol oxidase, and superoxide dismutase (SOD); examples of the transferase may include choline acetyltransferase and aspartate aminotransferase; examples of the hydrolase may include carbohydrase, esterase, protease, and amylase; examples of the lyase may include aldolase and hydrase; examples of the isomerase may include glucose-phosphate isomerase and glucose isomerase; and examples of the synthetase may include t-RNA synthetase and acetyl CoA synthetase.

The content of the enzyme in the stabilized enzyme composition of the present invention may be $10^{-10}$ to 10 wt %, preferably $10^{-7}$ to 1 wt %. With the enzyme content of not higher than 10 wt %, the hydrogel may exhibit excellent stabilizing effect, and the gel strength may be maintained.

The content of the hydrogel in the stabilized enzyme composition of the present invention may be 0.5 to 70 wt %, preferably 1 to 50 wt % in terms of the composition for hydrogel. With the hydrogel content of not lower than 0.5 wt %, excellent stabilizing effect of the hydrogel may be exhibited, whereas with the hydrogel content of not higher than 70 wt %, the enzyme activity is well expressed.

The stabilized enzyme composition of the present invention may be prepared by any method, for example, by gelating the composition for hydrogel using a solution of the above enzyme as an aqueous medium to thereby form a hydrogel. More specifically, in a solution containing the enzyme and one of the polymers from the composition for hydrogel, the other polymer from the composition for hydrogel is added to form a hydrogel in a solution, to thereby obtain a stabilized enzyme composition with excellent stability of enzyme activity, wherein the enzyme is enclosed in the hydrogel.

The composition for hydrogel according to the present invention contains a particular polymer that has substantially no reactive group capable of forming a chemically cross-linked structure, and a particular copolymer having a phosphorylcholine-like group. Thus the present composition is substantially water-soluble, is excellently safe, and is useful as a material for a hydrogel capable of enclosing drugs, biopolymers, and biological cells. Further, the present hydrogel may be obtained simply and conveniently by stirring the composition in an aqueous medium, has excellent biocompatibility originated from the copolymer having a phosphorylcholine-like group, and is substantially soluble in water at an ordinary temperature. Thus the present hydrogel is useful as a material for various cosmetic materials and dermal plasters.

The medical equipment and the clinical test instrument according to the present invention are provided with a coating of the dried hydrogel, and are thus given the various properties of the hydrogel. The equipment and instrument are excellent in biocompatibility such as inactivatability of blood constituents and non-adsorbability of biomaterials, and also have superior antifouling and moisturizing properties.

The enzyme stabilizer according to the present invention contains the hydrogel, so that the stabilizer may improve the stability of an enzyme by enclosing the enzyme therein.

The stabilized enzyme composition according to the present invention contains the hydrogel and an enzyme, so that the enzyme may be enclosed in the hydrogel to provide a highly stable enzyme formulation.

EXAMPLES

The present invention will be explained in more detail with reference to the Synthetic Examples, Examples, and Comparative Examples. However, the present invention is not limited thereto.

Measurements of the molecular weight of the polymers and the amount of impurities were made in accordance with the following method.

<Molecular Weight of polymers>

Molecular weight of the polymers were measured by gel permeation chromatography (GPC) employing a phosphate buffer (pH7.4, 20 mM) or methanol/chloroform (⅙ weight ratio) as an eluent and polyethylene glycols as standards. Detection was made by refractive index (RI).

<Analysis of Impurities>

Amount of the impurities was measured by the GPC with the same condition as the above GPC except that the detection was made by UV (210 nm or 260 nm).

Synthetic Example 1

Synthesis of ($MPC_{0.8}$-butyl $methacrylate_{0.2}$) copolymer 334.7 g of MPC was dissolved in 562.5 g of water and put in a four-necked flask. 40.3 g of butyl methacrylate was dissolved in 562.5 g of ethanol, and this solution was added to the MPC solution. The mixture was bubbled with nitrogen gas for 30 minutes. The mixture was then kept at 40° C. and admixed with 1.47 g of t-butyl peroxyneodecanoate, and polymerization reaction was performed for 4 hours. The temperature was then elevated to 60° C. and reaction was further performed for 2 hours, to obtain 1501 g of polymer liquid. The polymerization reaction ratio and molecular weight of the obtained polymer liquid were measured by GPC. As a result, the polymerization reaction ratio was 91.7% and the weight average molecular weight was 1210000.

750 g of the polymer liquid was added dropwise to 4 L of acetone/hexane (1/1 weight ratio) mixed solvent with stirring. The precipitate was recovered by filtration and dried in a vacuum at room temperature for 48 hours to prepare polymer powders. The obtained polymer powders were dissolved in 1 L of pure water. The solution was put in a dialysis membrane having molecular cutoff of 12000 (manufactured by Spectrapore Co.) and immersed in 10 L of pure water (dialysis liquid). The dialysis liquid was exchanged in every 24 hours for three times, i.e., the membrane separation treatment was performed for 96 hours. The purified solution thus obtained was mixed with pure water to adjust the polymer concentration to 5 wt %, to obtain a polymer liquid. The amount of the solid in the polymer liquid was 95.4 g and yield was 55.5%.

The ratio of the units corresponding to the polymerization unit (a) and polymerization unit (b) in the obtained polymer was measured by nuclear magnetic resonance (NMR) spectrum analysis. The results are shown in Table 1.

Synthetic Example 2

Synthesis of ($MPC_{0.3}$-butyl methacrylate$_{0.7}$ copolymer 84.6 g of MPC was dissolved in 486 g of water and put in a four-necked flask. 95.4 g of butyl methacrylate dissolved in 1134 g of ethanol, and this solution was added to the MPC solution. The mixture was bubbled with nitrogen gas for 30 minutes. The mixture was then kept at 50° C. and admixed with 4.40 g of t-butyl peroxyneodecanoate, and polymerization reaction was performed for 3 hours. The temperature was then elevated to 60° C. and reaction was further performed for 2 hours, to obtain 1804 g of polymer liquid. The polymerization reaction ratio and molecular weight of the obtained polymer were measured by GPC. As a result, the polymerization reaction ratio was 95.2% and the weight average molecular weight was 120000.

900 g of the polymer liquid was added dropwise to 4 L of acetone/hexane (1/1 weight ratio) mixed solvent with stirring. The precipitate was recovered by filtration and dried in a vacuum at room temperature for 48 hours to prepare polymer powders. The obtained polymer powders was dissolved in 1 L of pure water. The solution was put in a dialysis membrane having molecular cutoff of 3500 (manufactured by Spectrapore Co.) and immersed in 10 L of pure water (dialysis liquid). The dialysis liquid was exchanged in every 24 hours for three times, i.e., the membrane separation treatment was performed for 96 hours. The purified solution thus obtained was mixed with pure water to adjust the polymer concentration to 5 wt %, to obtain a polymer liquid. The amount of the solid in the polymer liquid was 53.6 g and yield was 62.6%.

The ratio of the units corresponding to the polymerization unit (a) and polymerization unit (b) in the obtained polymer was measured by NMR. The results are shown in Table 1.

Synthetic Example 3

Synthesis of MPC Homopolyer 600 g of MPC was dissolved in 900 g of water and put in a four-necked flask. The solution was bubbled with nitrogen gas for 30 minutes. The solution was then kept at 60° C. and admixed with 11.7 g of succinyl peroxide, and polymerization reaction was performed for 6 hours, to obtain 1511 g of polymer liquid. The polymerization reaction ratio and molecular weight of the obtained polymer were measured by GPC. As a result, the polymerization reaction ratio was 95.3% and the weight average molecular weight was 1030000.

The polymer liquid was diluted with 1500 ml of ion exchanged water. The solution was put in a dialysis membrane having molecular cutoff of 12000 (manufactured by Spectrapore Co.) and immersed in 15 L of pure water (dialysis liquid). The dialysis liquid was exchanged in every 24 hours for three times, i.e., the membrane separation treatment was performed for 96 hours. The purified solution thus obtained was mixed with pure water to adjust the polymer concentration to 5 wt %, to obtain a polymer liquid. The amount of the solid in the polymer liquid was 556.1 g and yield was 97.3%.

The ratio of the units corresponding to the polymerization unit (a) was 100%.

Synthetic Example 4

Synthesis of ($MPC_{0.2}$-butyl methacrylate$_{0.8}$) copolymer 102.5 g of MPC was dissolved in 360 g of water and put in a four-necked flask. 197.5 g of butyl methacrylate was dissolved in 840 g of ethanol, and this solution was added to the MPC solution. The mixture was bubbled with nitrogen gas for 30 minutes. The mixture was then kept at 60° C. and admixed with 0.37 g of t-butyl peroxyneodecanoate, and polymerization reaction was performed for 6 hours, to obtain 1500 g of polymer liquid. The polymerization reaction ratio and molecular weight of the obtained polymer were measured by GPC. As a result, the polymerization reaction ratio was 94.5% and the weight average molecular weight was 560000.

750 g of the polymer liquid was added dropwise to 4 L of diethyl ether with stirring. The precipitate was recovered by filtration and dried in a vacuum at room temperature for 48 hours to prepare polymer powders. The amount of the polymer powders was 99.4 g and yield was 70.1%.

The ratio of the units corresponding to the polymerization unit (a) and polymerization unit (b) in the obtained polymer was measured by NMR. The results are shown in Table 1.

Synthetic Example 5

Synthesis of ($MPC_{0.3}$-butyl methacrylate$_{0.2}$-methacrylic acid$_{0.5}$) copolymer 244.8 g of MPC was dissolved in 562.5 g of water. The solution was further admixed with 71.4 g of methacrylic acid and put in a four-necked flask. 58.8 g of butyl methacrylate was dissolved in 562.5 g of ethanol, and this solution was added to the MPC solution. The mixture was bubbled with nitrogen gas for 30 minutes. The mixture was then kept at 40° C. and admixed with 2.20 g of t-butyl peroxyneodecanoate, and polymerization reaction was performed for 3 hours. The temperature was then elevated to 60° C. and reaction was further performed for 2 hours, to obtain 1502 g of polymer liquid. The polymerization reaction ratio and molecular weight of the obtained polymer were measured by GPC. As a result, the polymerization reaction ratio was 95.4% and the weight average molecular weight was 726000.

The polymer liquid was added dropwise to 4 L of acetone/hexane (1/1 weight ratio) mixed solvent with stirring. The precipitate was recovered by filtration and dried in a vacuum at room temperature for 48 hours to prepare polymer powders. The obtained polymer powders was dissolved in 1 L of pure water. The solution was put in a dialysis membrane having molecular cutoff of 12000 (manufactured by Spectrapore Co.) and immersed in 10 L of pure water (dialysis liquid). The dialysis liquid was exchanged in every 24 hours for three times, i.e., the membrane separation treatment was performed for 96 hours. The purified solution thus obtained was mixed with pure water to adjust the polymer concentration to 5 wt %, to obtain a polymer liquid. The amount of the solid in the polymer liquid was 226.0 g and yield was 63.2%. Changing of concentration in the Examples that will be described later was made by dilution with pure water or condensation by evaporation.

The ratio of the units corresponding to the polymerization unit (a), polymerization unit (b) and polymerization unit (c) in the obtained polymer was measured by NMR. The results are shown in Table 1.

Synthetic Example 6

Synthesis of ($MPC_{0.9}$-methacrylic $acid_{0.2}$) copolymer 348.7 g of MPC was dissolved in 1440 g of pure water. The solution was further admixed with 11.3 g of methacrylic acid and put in a four-necked flask. The mixture was bubbled with nitrogen gas for 30 minutes. The mixture was then kept at 70° C. and admixed with 7.02 g of succinyl peroxide, and polymerization reaction was performed for 6 hours, to obtain 1807 g of polymer liquid. The polymerization reaction ratio and molecular weight of the obtained polymer were measured by GPC. As a result, the polymerization reaction ratio was 99.3% and the weight average molecular weight was 440000.

The polymer liquid was put in a dialysis membrane having molecular cutoff of 12000 (manufactured by Spectrapore Co.) and immersed in 10 L of pure water (dialysis liquid). The dialysis liquid was exchanged in every 24 hours for three times, i.e., the membrane separation treatment was performed for 96 hours. The purified solution thus obtained was mixed with pure water to adjust the polymer concentration to 5 wt %, to obtain a polymer liquid. The amount of the solid in the polymer liquid was 350.7 g and yield was 98.1%. Changing of concentration in the Examples that will be described later was made by dilution with pure water or condensation by evaporation.

The ratio of the units corresponding to the polymerization unit (a) and polymerization unit (c) in the obtained polymer was measured by NMR. The results are shown in Table 1.

Synthetic Example 7

Synthesis of ($MPC_{0.9}$-stearyl $methacrylate_{0.2}$) copolymer 318.6 g of MPC and 41.4 g of stearyl methacrylate were dissolved in 1440 g of ethanol and put in a four-necked flask. The mixture was bubbled with nitrogen gas for 30 minutes. The mixture was then kept at 50° C. and admixed with 7.81 g of t-butyl peroxyneodecanoate, and polymerization reaction was performed for 3 hours. The temperature was then elevated to 60° C. and reaction was further performed for 2 hours, to obtain 1807 g of polymer liquid. The polymerization reaction ratio and molecular weight of the obtained polymer were measured by GPC. As a result, the polymerization reaction ratio was 98.7% and the weight average molecular weight was 140000.

The polymer liquid was added dropwise to 8 L of diethyl ether with stirring. The precipitate was recovered by filtration and dried in a vacuum at room temperature for 48 hours to prepare polymer powders. The obtained polymer powders was dissolved in 1 L of pure water. The solution was put in a dialysis membrane having molecular cutoff of 3500 (manufactured by Spectrapore Co.) and immersed in 10 L of pure water (dialysis liquid). The dialysis liquid was exchanged in every 24 hours for three times, i.e., the membrane separation treatment was performed for 96 hours. The purified solution thus obtained was mixed with pure water to adjust the polymer concentration to 5 wt %, to obtain a polymer liquid. The amount of the solid in the polymer liquid was 243.8 g and yield was 68.6%. Changing of concentration in the Examples that will be described later was made by dilution with pure Water or condensation by evaporation.

The ratio of the units corresponding to the polymerization unit (a) and polymerization unit (b) in the obtained polymer was measured by NMR. The results are shown in Table 1.

Synthetic Example 8

Synthesis of ($MPC_{0.5}$-methacrylic $acid_{0.5}$) copolymer 278.7 g of MPC was dissolved in 1440 g of pure water. The solution was further admixed with 81.3 g of methacrylic acid and put in a four-necked flask. The mixture was bubbled with nitrogen gas for 30 minutes. The mixture was then kept at 70° C. and admixed with 14.04 g of succinyl peroxide, and polymerization reaction was performed for 6 hours, to obtain 1814 g of polymer liquid. The polymerization reaction ratio and molecular weight of the obtained polymer were measured by GPC. As a result, the polymerization reaction ratio was 96.2% and the weight average molecular weight was 1100000.

The polymer liquid was put in a dialysis membrane having molecular cutoff of 12000 (manufactured by Spectrapore Co.) and immersed in 10 L of pure water (dialysis liquid). The dialysis liquid was exchanged in every 24 hours for three times, i.e., the membrane separation treatment was performed for 96 hours. The purified solution thus obtained was mixed with pure water to adjust the polymer concentration to 5 wt %, to obtain a polymer liquid. The amount of the solid in the polymer liquid was 321.4 g and yield was 92.8%. Changing of concentration in the Examples that will be described later was made by dilution with pure water or condensation by evaporation.

The ratio of the units corresponding to the polymerization unit (a) and polymerization unit (c) in the obtained polymer was measured by NMR. The results are shown in Table 1.

TABLE 1

|  | Content of each unit in the copolymer (mol %) | | |
| --- | --- | --- | --- |
|  | Unit (a) | Unit (b) | Unit (c) |
| Synthetic Example 1 | 80 | 20 | — |
| Synthetic Example 2 | 30 | 70 | — |
| Synthetic Example 3 | 100 | — | — |
| Synthetic Example 4 | 20 | 80 | — |
| Synthetic Example 5 | 30 | 20 | 50 |
| Synthetic Example 6 | 90 | — | 10 |
| Synthetic Example 7 | 90 | 10 | — |
| Synthetic Example 8 | 50 | — | 50 |

Examples 1-1 and 1-2

Preparation of Hydrogel Consisting of Polymer Having Phosphorylcholine-Like Group and Acrylic Acid Homopolymer A composition for hydrogel consisting of 10 g of aqueous solution prepared in Synthetic Example 1 or 2 containing 5 wt % of copolymer and 10 g of 2 wt % acrylic acid homopolymer solution (weight average molecular weight of the acrylic acid homopolymer was 1000000) was prepared. The composition was thoroughly stirred in a 50 ml glass vessel, to prepare a colorless uniform hydrogel. The Example in which the solution obtained in Synthetic Example 1 was employed is referred to as Example 1-1, and the Example in which the solution obtained in Synthetic Example 2 is referred to as Example 1-2.

For the obtained hydrogel, evaluation of state after stirring, re-fluidization evaluation by heating, and solubility evaluation in water was performed in accordance with the following. The results are shown in Table 2.

<Evaluation of State after Stirring>

The hydrogel after stirring was left stand for 10 minutes and the vessel was inclined 90°. The fluidity of the hydrogel was visually observed.

<Re-Fluidization Evaluation by Heating>

The obtained hydrogel which was fluidized when heated to 90° C. and re-gelated when re-cooled to the ordinary temperature was evaluated as "Good". The hydrogel which was not fluidized when heated to 90° C. or which did not re-gelated when re-cooled to the ordinary temperature was evaluated as "Bad".

<Solubility Evaluation in Water>

The obtained hydrogel was left stand in 500 g of pure water at room temperature. The hydrogel which was dissolved after 24 hours was evaluated as "Good", and the hydrogel which was not dissolved was evaluated as "Bad".

Comparative Example 1-1

Preparation of Hydrogel Consisting of Polymer Having Phosphorylcholine-Like Group and Acrylic Acid Homopolymer 10 g of aqueous solution prepared in Synthetic Example 3 containing 5 wt % of MPC homopolymer and 10 g of 2 wt % acrylic acid homopolymer solution (weight average molecular weight of the acrylic acid homopolymer was 1000000) were mixed and thoroughly stirred in a 50 ml glass vessel. As a result, white precipitate was generated but no gelation was observed. For the obtained precipitate, evaluations were made in the same manner as in Examples 1-1 and 1-2. The results are shown in Table 2.

Comparative Example 1-2

Preparation of Hydrogel Consisting of Polymer Having Phosphorylcholine-Like Group and Acrylic Acid Homopolymer To 5 g of powders prepared in Synthetic Example 4, 100 g of water were added and stirred. However, the powder was not miscible.

10 g of the obtained stirred product and 10 g of 2 wt % acrylic acid homopolymer solution (weight average molecular weight of the acrylic acid homopolymer was 1000000) were mixed in a 50 ml glass vessel. However, thorough mixture was not obtainable.

The obtained product was evaluated in the same manner as in Examples 1-1 and 1-2. The results are shown in Table 2.

TABLE 2

| | Composition | Weight ratio of (1):(2) | State after stirring | Re-fluidization by heating to 90° C. | Solubility in water |
|---|---|---|---|---|---|
| Example 1-1 | (1) Syn. Example 1 (2) PAA | 5:2 | Gelation | Good | Good |
| Example 1-2 | (1) Syn. Example 2 (2) PAA | 5:2 | Gelation | Good | Good |

TABLE 2-continued

| | Composition | Weight ratio of (1):(2) | State after stirring | Re-fluidization by heating to 90° C. | Solubility in water |
|---|---|---|---|---|---|
| Comparative Example 1-1 | (1) Syn. Example 3 (2) PAA | 5:2 | Precipitation | Bad | Bad |
| Comparative Example 1-2 | (1) Syn. Example 4 (2) PAA | 5:2 | not miscible (ununiform). | Bad | Bad |

PAA: Acrylic acid homopolymer

Examples 2-1 and 2-2

Preparation of Hydrogel Consisting of Polymer Having Phosphorylcholine-Like Group and (polyethylene glycol-polypropylene glycol) block copolymer A composition for hydrogel consisting of 10 g of aqueous solution prepared in Synthetic Example 5 or 6 containing 10 wt % of copolymer and 10 g of 5 wt % (polyethylene glycol-polypropylene glycol) block copolymer solution (weight average molecular weight of the copolymer was 31000) was prepared. The composition was thoroughly stirred in a 50 ml glass vessel, to prepare a colorless uniform hydrogel. The Example in which the solution obtained in Synthetic Example 5 was employed is referred to as Example 2-1, and the Example in which the solution obtained in Synthetic Example 6 is referred to as Example 2-2.

For the obtained hydrogel, evaluations were performed in the same manner as in Examples 1-1 and 1-2. The results are shown in Table 3.

Comparative Examples 2-1 and 2-2

Preparation of Hydrogel Consisting of Polymer Having Phosphorylcholine-Like Group and (polyethylene glycol-polypropylene glycol) block copolymer 10 g of aqueous solution prepared in Synthetic Example 3 containing 5 wt % of the polymer or 10 g of stirred product (not uniformly mixed) containing 5 wt % of polymer prepared in Synthetic Example 4 was stirred with 10 g of 5 wt % (polyethylene glycol-polypropylene glycol) block copolymer solution (weight average molecular weight of the copolymer was 31000) in a 50 ml glass vessel. However, viscosity was not elevated and gel was not observed. The Example in which the solution obtained in Synthetic Example 3 was employed is referred to as Comparative Example 2-1, and the Example in which the solution obtained in Synthetic Example 4 is referred to as Comparative Example 2-2. The results are shown in Table 3.

TABLE 3

| | Composition | Weight ratio of (1):(2) | State after stirring | Re-fluidization by heating to 90° C. | Solubility in water |
|---|---|---|---|---|---|
| Example 2-1 | (1) Syn. Example 5 (2) PEG-PPG | 2:1 | Gelation | Good | Good |

TABLE 3-continued

| | Composition | Weight ratio of (1):(2) | State after stirring | Refluidization by heating to 90° C. | Solubility in water |
|---|---|---|---|---|---|
| Example 2-2 | (1) Syn. Example 6 (2) PEG-PPG | 2:1 | Gelation | Good | Good |
| Comparative Example 2-1 | (1) Syn. Example 3 (2) PEG-PPG | 1:1 | No change | — | — |
| Comparative Example 2-2 | (1) Syn. Example 4 (2) PEG-PPG | 1:1 | not miscible (ununiform) | — | — |

PEG-PPG: Polyethylene glycol-polypropylene glycol block copolymer

Examples 3-1 to 3-4
Preparation of Hydrogel Consisting of Polymer Having Phosphorylcholine-Like Group A composition for hydrogel consisting of 10 g of copolymer aqueous solution prepared in Synthetic Example 5 or 6 having a concentration shown in Table 4 and 10 g of 5 wt % copolymer solution prepared in Synthetic Example 7 was prepared. The composition was thoroughly stirred in a 50 ml glass vessel, to prepare a colorless uniform hydrogel. For the obtained hydrogels, evaluations were performed in the same manner as in Examples 1-1 and 1-2. The results are shown in Table 4.

Comparative Example 3-1

Preparation of Hydrogel Consisting of Polymer Having Phosphorylcholine-Like Group 10 g of 5 wt % MPC homopolymer aqueous solution prepared in Synthetic Example 3 and log of 5 wt % copolymer aqueous solution prepared in Synthetic Example 7 were stirred in a 50 ml glass vessel. The liquid remained colorless and no change was observed. No gel was generated.

TABLE 4

| | Composition | Weight ratio of (1):(2) | State after stirring | Refluidization by heating to 90° C. | Solubility in water |
|---|---|---|---|---|---|
| Example 3-1 | (1) Syn. Example 5 (Concentration 5 wt %) (2) Syn. Example 7 | 1:1 | Gelation | Good | Good |
| Example 3-2 | (1) Syn. Example 5 (Concentration 60 wt %) (2) Syn. Example 7 | 12:1 | Gelation | Good | Good |
| Example 3-3 | (1) Syn. Example 6 (Concentration 5 wt %) (2) Syn. Example 7 | 1:1 | Gelation | Good | Good |
| Example 3-4 | (1) Syn. Example 6 (Concentration 60 wt %) (2) Syn. Example 7 | 12:1 | Gelation | Good | Good |
| Comparative Example 3-1 | (1) Syn. Example 3 (2) Syn. Example 7 | 1:1 | No change | — | — |

Example 4
Evaluation of Moisturizing Ability of High Molecular Hydrogel Having Phosphorylcholine-Like Group A composition for hydrogel consisting of 1:1 weight ratio of the 5 wt % copolymer aqueous solution prepared in Synthetic Example 7 and the 5 wt % copolymer aqueous solution prepared in Synthetic Example 8 was prepared. The composition was stirred to prepare a hydrogel.

The hydrogel thus obtained was subjected to organic keratin application test with reference to J. Jap. Oil Chem. Soc. vol. 48 (p577, 1999).

That is, 0.2 g of the hydrogel was attached to medial side of left forearm of a human and spread thereon over the diameter of 3 cm. 50 minutes after spreading, the applied portion was washed with water. Moisture of the skin was measured three times at 50 minutes after spreading, immediately after washing and 2 hours after washing. Measurement was performed by 3.5 MHz high-frequency electric conductivity measurement device (manufactured by IBS Co.). Average of 5 subjects was calculated. The results are expressed as ratio with respect to moisture on the skin before hydrogel application being 1. As a control, moisture of skin surface without application of hydrogel was also measured. The results are shown in Table 5.

TABLE 5

| | Moisture of skin (relative value) | |
|---|---|---|
| Operation | Surface without hydrogel application | Surface with hydrogel application |
| 50 minutes after application of hydrogel | 1.00 | 1.80 |
| Immediately after skin washing | 1.55 | 2.20 |
| Two hours after washing | 1.15 | 2.45 |

From the results in Table 5, it was confirmed that moisture holding ability of skin was improved by application of the hydrogel of the skin surface. That is, the hydrogel has an ideal effect as cosmetic moisturizer.

Example 5
Preparation of Dermal Plaster Material (Wound Dressing Material) Containing High Molecular Hydrogel Having Phosphorylcholine-Like Group and Evaluation Thereof A composition for hydrogel consisting of 1:1 weight ratio of the 0.5 wt % copolymer aqueous solution prepared in Synthetic Example 7 and the 0.5 wt % copolymer aqueous solution prepared in Synthetic Example 8. The composition was stirred to prepare a solution. Japanese pharmacopoeia gauze was immersed in the obtained solution to absorb the solution. Subsequently, the gauze was dried at 90° C. for two hours and then at 110° C. for one hour to prepare a MPC containing gauze.

The MPC containing gauze thus obtained was swelled with physiological saline for 15 minutes to form a hydrogel in the gauze, and then subjected to the following wound dressing ability evaluation. The results are shown in Table 6.
<Evaluation of Wound Dressing Ability>

Five ddy mice (femele, 6 week old, body weight 25 to 30 g) per one group were employed as subject animals. Mice were shaved under Nembutal anesthesia. A full-thickness dermal defective wound was made on the skin on posterior median line with surgical scissors. Immediately after producing the open wound, the hydrogel containing gauze was applied thereon and fixed by wrapping with a stretchable bandage. After forming the defective wound, the dressing material was exchanged once in a day and degree of bleeding upon removing the old dressing material for changing was evaluated in four degrees (0: no bleeding, 1: slight bleeding, 2: moderate bleeding, 3: significant bleeding). Average of 5 animals was determined by visual observation. As a control, untreated Japanese pharmacopoeia gauze was immersed in physiological saline for 15 minutes and subjected to the same evaluation.

TABLE 6

|  | Number of days lapsed | | | | |
| --- | --- | --- | --- | --- | --- |
|  | 1 | 2 | 3 | 4 | 5 |
| MPC treated | 0.8 | 0.4 | 0.2 | 0.1 | 0.1 |
| Untreated | 2.2 | 2.6 | 2.6 | 2.8 | 2.6 |

From the results in Table 6, it was confirmed that the gauze with the hydrogel has higher ability to prevent adhesion of blood coagulates than the untreated gauze, and bleeding on the wound may be prevented.

Example 6
Evaluation of Blood Compatibility and Surface Lubricity of Medical Equipment with Coating of High Molecular Hydrogel Having Phosphorylcholine-Like Group A composition for hydrogel consisting of 1:1 weight ratio of the 0.5 wt % copolymer aqueous solution prepared in Synthetic Example 7 and the 0.5 wt % copolymer aqueous solution prepared in Synthetic Example 8. The composition was stirred to prepare a solution. A medical guidewire having a urethane surface which had been pre-treated with 0.1N—NaOH for 15 minutes was coated with the solution. The coated guidewire and uncoated guidewire were dried by heating at 90° C. for 3 hours. On the surface of the coated guidewire, a layer of the dried hydrogel was formed. Each guidewire was cut to form pieces having a length of 2 cm. The pieces were put in a 2 ml tube with a cap made of polypropylene, and stored by immersing them with 0.1 M phosphate buffer until just before beginning the test.

As a blood compatibility evaluation, platelet adhesion test was performed as follows.

1 vol % of 0.1 wt % sodium citrate aqueous solution was added to rabbit blood. The mixture was then centrifuged at 37° C. at 750 rpm for 15 minutes, to obtain a platelet rich plasma. The platelet rich plasma thus obtained was diluted two times with 0.1M phosphate buffer and placed at 37° C. The plasma was used so that the following procedure was finished within 2 hours.

From the tube with the cap made of polypropylene, the phosphate buffer was removed. To the tube containing the guidewire, the diluted platelet rich plasma was added and left stand at 37° C. for 15 minutes. The guidewire was then taken and washed softly with 0.1M phosphate buffer. The attached platelet was then fixed with 0.1 wt % glutaraldehyde aqueous solution, washed with ethanol/water mixed liquid, and dried. The number of platelets attached on the surface of each guidewire thus obtained and state of adhesion were observed with a scanning electron microscope (JEOL Ltd.), and comparison between the uncoated guidewire and the coated guidewire was performed.

As a result, a lot of the platelets adhered were observed on the uncoated guidewire. On the other hand, few platelets were observed on the coated guidewire, and the form of the slightly adhered platelets was non-deformed and in an inactivated state.

The surface lubricity of the obtained guidewire material was measured as a friction coefficient in the physiological saline with a friction tester (Kato Tech K.K.).

As a result, the coated guidewire exhibited the friction coefficient that was $1/12$ that of uncoated guidewire. Thus, a great improvement of the surface lubricity was confirmed.

Example 7
Evaluation of High Molecular Hydrogel Having Phosphorylcholine-Like Group Coated on Clinical Test Instrument A composition for hydrogel consisting of 10 g of the 0.1 wt % copolymer aqueous solution prepared in Synthetic Example 7 and 10 g of the 0.1 wt % copolymer aqueous solution prepared in Synthetic Example 8. The composition was stirred to prepare a hydrogel. The obtained hydrogel was dissolved at 90° C. 300l each of the fluidized gel was put in each well of a polystyrene 96 well multiplate. The plate was dried at 60° C. for 24 hours, to form a test plate with dried hydrogel coating on the surface of each well.

Bovine serum albumin as a protein was dissolved at 40 mg/ml in a phosphate buffer. 300 $\mu$l each of the resulting phosphate-buffered solution of bovine serum albumin was put in each well of the test plate and left stand for 5 minutes. Subsequently, the solution was removed from the wells. The wells were washed twice with 300 $\mu$l of 0.1 M phosphate buffer. The amount of the protein adsorbed on each cell was quantified with Micro BCA protein Assay kit (manufactured by PIERCE Co.). As a control, the same test was performed with a plate that had not treated with hydrogel.

As a result, adsorption of bovine serum albumin on the test plate treated with hydrogel was 0.1 $\mu$g/cm$^2$ or less, while adsorption of bovine serum albumin on the plate without hydrogel treatment was 1.5 $\mu$g/cm$^2$. Therefore, it was confirmed that the adsorption of protein can be inhibited with the hydrogel of the present invention.

Example 8

Enclosing and Sustained Release of Protein Using High Molecular Hydrogel Having Phosphorylcholine-Like Group To 9 g of the 5 wt % copolymer aqueous solution prepared in Synthetic Example 7, 2 ml of 40 mg/ml bovine serum albumin solution was added, to which 9 g of the 5 wt % copolymer aqueous solution prepared in Synthetic Example 8 was further added. The mixture was gently stirred to prepare a hydrogel enclosing bovine serum albumin.

The obtained gel was put in a dialysis membrane having molecular cutoff of 120000 and immersed in 200 ml of 100 mM phosphate buffer. The temperature was kept at 37° C. and the outer dialysis liquid was taken in every one hour.

Release of albumin from the hydrogel was quantified by ninhydrin method.

As a control sample, 2 ml of the bovine serum albumin solution in 18 ml of 100 mM phosphate buffer put in the dialysis membrane, and 20 g of 1 wt % agarose gel enclosing 80 mg of bovine serum albumin were subjected to the evaluation.

As the hydrogel in the phosphate buffer slowly disintegrated, release of bovine serum albumin was observed. Eight hours after onset of dialysis, release of albumin was 24% of the control with bovine serum albumin solution itself put in the dialysis membrane and 80% of the control with the agarose gel enclosing bovine serum albumin. Therefore, it was confirmed that the high molecular hydrogel having the phosphorylcholine-like group enclosing albumin exhibits sustained release of the protein.

Example 9

Stabilized Enzyme Composition Using High Molecular Hydrogel Having Phosphorylcholine-Like Group The polymer solution containing 5 wt % of the polymer prepared in Synthetic Example 1 was diluted with Dulbecco's phosphate buffered saline solution and pH was adjusted to 7.4, to prepare a solution containing 2 wt % of polymer. To the solution, horse radish peroxidase (referred to hereinbelow as HRP) was dissolved at 1.33 μg/ml, to prepare a polymer/enzyme solution (referred to hereinbelow as enzyme solution 1).

The polymer solution containing 5 wt % of the polymer prepared in Synthetic Example 8 was diluted with Dulbecco's phosphate buffered saline solution (pH=approximately 4.0), to prepare a solution containing 2 wt % of polymer (referred to hereinbelow as solution 2).

The enzyme solution 1 and the solution 2 were mixed at 3:1 weight ratio, to prepare a stabilized enzyme composition in which the gel encloses the enzyme. The stabilized enzyme composition was stored at 37° C.

Immediately after the preparation, and 2 days, 3 days and 6 days after the preparation, a portion of the stabilized enzyme composition was taken and diluted with 9 times volume of the Dulbecco's phosphate buffered saline (pH= 7.4) to dissolve the gel, and the activity of HRP was measured. Measurement of the activity was performed by colorimetry at the wavelength of 405 nm using 2,2'-azino-di(3-ethylbenzthiazoline-6-sulfonate) as a substrate. Percentage of the enzyme activity in each sample with respect to the enzyme activity of the sample taken immediately after preparing the stabilized enzyme composition was calculated. The results are shown in Table 7.

Comparative Example 4

HRP was dissolved in Dulbecco's phosphate buffered saline (pH=7.4) at 1 μg/ml to prepare a HRP solution. Immediately after the preparation and 2 days, 3 days and 6 days after the preparation, a portion of the HRP solution was taken and diluted with 9 times volume of the Dulbecco's phosphate buffered saline (pH=7.4), and the HRP activity was measured in the same manner as in Example 9. Percentage of the enzyme activity in each sample with respect to the enzyme activity of the sample taken immediately after preparing the HRP solution was calculated. The results are shown in Table 7.

TABLE 7

| Number of days | Enzyme activity (%) | | | |
|---|---|---|---|---|
| | 0 day | 2 days | 3 days | 6 days |
| Example 9 | 100 | 102 | 92 | 92 |
| Comparative Example 4 | 100 | 0 | 0 | 0 |

What is claimed is:

1. A composition for hydrogel substantially soluble in water at an ordinary temperature comprising:

a copolymer (A1) having a phosphorylcholine-like group soluble in an aqueous medium, said copolymer (A1) comprising 25 to 97 mol % of unit (a) derived from at least one of compounds represented by the formula (1) having a phosphorylcholine-like group, and 3 to 75 mol % of unit (b) derived from at least one hydrophobic monomer represented by the formula (2); and a polymer (B) other than said copolymer (A1) soluble in an aqueous medium having one or more of hydrophilic groups selected from the soup consisting of a hydroxyl group, a carboxyl group, a phosphonic acid group, a sulfonic acid group, an amide group, an amino group, a dialkylamino group, a trialkylammonium salt group, a trialkylphosphonium salt group and a polyoxyethylene group:

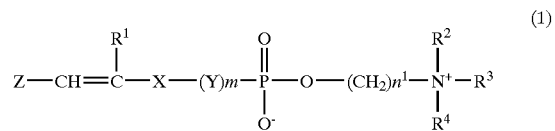

(1)

wherein X represents a divalent organic residue, Y represents an alkyleneoxy group having 1 to 6 carbon atoms, Z represents a hydrogen atom or a group $R^5$—O—CO—(wherein $R^5$ represents an alkyl group having 1 to 10 carbon atoms or a hydroxyalkyl group having 1 to 10 carbon atoms), $R^1$ represents a hydrogen atom or a methyl group, $R^2$, $R^3$ and $R^4$ are the same or different groups and each represents a hydrogen atom or a hydrocarbon or hydroxyhydrocarbon group having 1 to 6 carbon atoms, m is 0 or 1, and $n^1$ is an integer of 2 to 4;

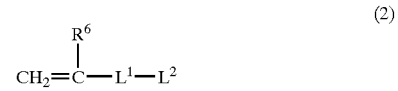

(2)

wherein R represents a hydrogen atom or a methyl group, $L^1$ represents —$C_6H_4$—, —(C=O)—O— —O—, —(C=O)NH—, —O—(C=O)— or —O—(C=O)—O— and $L^2$ represents a hydrophobic functional group selected from a hydrogen atom, —$(CH_2)_{n^2}$-$L^3$ and —$((CH_2)p\text{-}O)$—$L^3$, wherein $n^2$ is an integer of 1 to 24, p is an integer of 3 to 5 and $L^3$ represents a hydrogen atom, a methyl group, —$C_6H_5$ or —O—$C_6H_5$;

wherein a combination of said copolymer (A1) and said polymer (B) is selected from the group consisting of 2-(meth)acryloyloxyethyl-2'-(trimethylammonio)ethyl phosphate-butyl (meth)acrylate copolymer and (meth) acrylic acid homopolymer; 2-(meth) acryloyloxyethyl-2'-(trimethylammonio)ethyl phosphate-butyl (meth)

acrylate copolymer and (meth)acrylic acid-methyl (meth) acrylate copolymer; 2-(meth)acryloyloxyethyl-2'-(trimethylammonio)ethyl phosphate-butyl (meth) acrylate copolymer and (meth)acrylic acid-ethyl(meth) acrylate copolymer; 2-(meth)acryloyloxyethyl-2'-(trimethylammonio)ethyl phosphate-butyl (meth) acrylate copolymer and (meth)acrylic acid-n-butyl (meth)acrylate copolymer; 2-(meth)acryloyloxyethyl-2'-(trimethylammonio)ethyl phosphate-butyl(meth) acrylate copolymer and (meth)acrylic acid-2-ethylhexyl (meth)acrylate copolymer; 2-(meth) acryloyloxyethyl-2'-(trimethylammonio) ethyl phosphate-butyl methacrylate copolymer and (meth) acrylic acid-lauryl (meth)acrylate copolymer; 2-(meth) acryloyloxyethyl-2'-(trimethylammonio)ethyl phosphate-butyl (meth)acrylate copolymer and (meth) acrylic acid-stearyl (meth)acrylate copolymer; 2-(meth)acryloyloxyethyl-2'-(trimethylammonio) ethyl phosphate-butyl (meth)acrylate copolymer and (meth) acrylic acid-benzyl (meth)acrylate copolymer; 2-(meth)acryloyloxyethyl-2'-(trimethylammonio)ethyl phosphate-butyl (meth)acrylate copolymer and (meth) acrylic acid-styrene copolymer; 2-(meth) acryloyloxyethyl-2'-(trimethylammonio)ethyl phosphate-lauryl (meth)acrylate copolymer and (meth) acrylic acid homopolymer; 2-(meth) acryloyloxyethyl-2'-(trimethylammonio)ethyl phosphate-lauryl (meth) acrylate copolymer and (meth)acrylic acid-methyl (meth) acrylate copolymer; 2-(meth)acryloyloxyethyl-2'-(trimethylammonio)ethyl phosphate-lauryl (meth) acrylate copolymer and (meth)acrylic acid-ethyl (meth) acrylate copolymer; 2-(meth)acryloyloxyethyl-2'-(trimethylammonio) ethyl phosphate-lauryl (meth) acrylate copolymer and (meth) acrylic acid-n-butyl (meth)acrylate copolymer; 2-(meth) acryloyloxyethyl-2'-(trimethylammonio)ethyl phosphate-lauryl (meth) acrylate copolymer and (meth)acrylic acid-2-ethylhexyl (meth)acrylate copolymer; 2-(meth) acryloyloxyethyl-2'-(trimethylammonio)ethyl phosphate-lauryl (meth)acrylate copolymer and (meth) acrylic acid-lauryl (meth)acrylate copolymer; 2-(meth) acryloyloxyethyl-2'-(trimethylammonio) ethyl phosphate-lauryl (meth)acrylate copolymer and (meth) acrylic acid-stearyl (meth)acrylate copolymer; 2-(meth) acryloyloxyethyl-2'-(trimethylammonio)ethyl phosphate-lauryl (meth)acrylate copolymer and (meth) acrylic acid-benzyl (meth) acrylate copolymer; 2-(meth)acryloyloxyethyl-2'-(trimethylammonio)ethyl phosphate-lauryl (meth)acrylate copolymer and (meth) acrylic acid-styrene copolymer; 2-(meth) acryloyloxyethyl-2'-(trimethylammonio)ethyl phosphate-stearyl (meth)acrylate copolymer and (meth)acrylic acid homopolymer; 2-(meth) acryloyloxyethyl-2'-(trimethylammonio)ethyl phosphate-stearyl (meth)acrylate copolymer and (meth)acrylic acid-methyl (meth)acrylate copolymer; 2-(meth)acryloyloxyethyl-2'-(trimethylammonio)ethyl phosphate-stearyl (meth)acrylate copolymer and (meth)acrylic acid-ethyl (meth)acrylate copolymer; 2-(meth)acryloyloxyethyl-2'-(trimethylammonio)ethyl phosphate-stearyl (meth)acrylate copolymer and (meth)acrylic acid-n-butyl (meth)acrylate copolymer, 2-(meth)acryloyloxyethyl-2'-(trimethylammonio)ethyl phosphate-stearyl (meth)acrylate copolymer and (meth)acrylic acid-2-ethylhexyl (meth)acrylate copolymer; 2-(meth) acryloyloxyethyl-2'-(trimethylammonio) ethyl phosphate-stearyl (meth)acrylate copolymer and (meth) acrylic acid-lauryl (meth)acrylate copolymer, 2-(meth) acryloyloxyethyl-2'-(trimethylammonio)ethyl phosphate-stearyl (meth)acrylate copolymer and (meth)acrylic acid-stearyl (meth) acrylate copolymer; 2(meth)acryloyloxyethyl-2'-(trimethylammonio)ethyl phosphate-stearyl (meth)acrylate copolymer and (meth)acrylic acid-benzyl (meth)acrylate copolymer; 2-(meth)acryloyloxyethyl-2'-(trimethylammonio) ethyl phosphate-stearyl (meth)acrylate copolymer and (meth) acrylic acid-styrene copolymer; 2-(meth) acryloyloxyethyl-2'-(trimethylammonio)ethyl phosphate-benzyl (meth)acrylate copolymer and (meth)acrylic acid homopolymer; 2-(meth) acryloyloxyethyl-2'-(trimethylammonio)ethyl phosphate-benzyl (meth)acrylate copolymer and (meth)acrylic acid-methyl (meth) acrylate copolymer, 2-(meth)acryloyloxyethyl-2'-(trimethylammonio)ethyl phosphate-benzyl (meth)acrylate copolymer and (meth)acrylic acid-ethyl (meth)acrylate copolymer; 2-(meth)acryloyloxyethyl-2'-(trimethylammonio)ethyl phosphate-benzyl (meth)acrylate copolymer and (meth)acrylic acid-n-butyl (meth)acrylate copolymer; 2-(meth)acryloyloxyethyl-2'-(trimethylammonio)ethyl phosphate-benzyl (meth)acrylate copolymer and (meth)acrylic acid-2-ethylhexyl (meth)acrylate copolymer; 2-(meth)acryloyloxyethyl-2'-(trimethylammonio) ethyl phosphate-benzyl (meth)acrylate copolymer and (meth) acrylic acid-lauryl (meth)acrylate copolymer; 2-(meth) acryloyloxyethyl-2'-(trimethylammonio)ethyl phosphate-benzyl (meth)acrylate copolymer and (meth)acrylic acid-stearyl (meth) acrylate copolymer; 2-(meth)acryloyloxyethyl-2'-(trimethylammonio)ethyl phosphate-benzyl (meth)acrylate copolymer and (meth)acrylic acid-benzyl (meth)acrylate copolymer; 2-(meth)acryloyloxyethyl-2'-(trimethylammonio) ethyl phosphate-benzyl (meth)acrylate copolymer and (meth) acrylic acid-styrene copolymer; 2-(meth) acryloyloxyethyl-2'-(trimethylammonio)ethyl phosphate-styrene copolymer and (meth) acrylic acid homopolymer; 2-(meth)acryloyloxyethyl-2'-(trimethylammonio)ethyl phosphate-styrene copolymer and (meth) acrylic acid-n-butyl (meth)acrylate copolymer; 2-(meth) acryloyloxyethyl-2'-(trimethylammonio)ethyl phosphate-styrene copolymer and (meth)acrylic acid-2-ethylhexyl (meth) acrylate copolymer; 2-(meth)acryloyloxyethyl-2'-(trimethylammonio) ethyl phosphate-styrene copolymer and (meth)acrylic acid-lauryl (meth) acrylate copolymer; 2-(meth)acryloyloxyethyl-2'-(trimethylammonio)ethyl phosphate-styrene copolymer and (meth) acrylic acid-stearyl (meth)acrylate copolymer; 2-(meth) acryloyloxyethyl-2'-(trimethylammonio)ethyl phosphate-styrene copolymer and (meth)acrylic acid-benzyl (meth)acrylate copolymer; and 2-(meth)acryloyloxyethyl-2'-(trimethylammonio) ethyl phosphate-styrene copolymer and (meth)acrylic acid-styrene copolymer.

2. A hydrogel substantially soluble in water at an ordinary temperature prepared by stirring the composition for hydrogel of claim 1 in an aqueous medium to gelate the composition.

3. The hydrogel of claim 2 further comprising therein one or more members selected from the group consisting of a drug, a biopolymer other than said copolymer (A1) and said polymer (B), and a biological cell.

4. The composition of claim 1 wherein a ratio of said copolymer (A1) to polymer (B) is 1:15 to 15:1 in weight ratio.

5. A composition for hydrogel substantially soluble in water at an ordinary temperature comprising:

a copolymer (A2) having a phosphorylcholine-like group soluble in an aqueous medium, said copolymer (A2) comprising 30 to 90 mol % of unit (a) derived from at least one compound represented by the formula (1) having a phosphorylcholine-like group, and 10 to 70 mol % of unit (c) other than said unit (a) derived from a monomer having one or more hydrophilic soups selected from the group consisting of a hydroxyl group, a carboxyl group, a phosphonic acid group, a sulfonic acid group, an amide group, an amino group, a dialkylamino group, a trialkylammonium salt group, a trialkylphosphonium salt group and a polyoxyethylene group; and a polymer (C) soluble in an aqueous medium having a hydrophobic functional group represented by —(CH$_2$)q-L$^4$ and/or —(CH$_2$)r-O)q-L$^4$, wherein L$^4$ represents an hydrogen atom, a methyl group, —C$_6$H$_5$ or —O—C$_6$H$_5$, q is an integer of 1 to 24, and r is an integer of 3 to 5

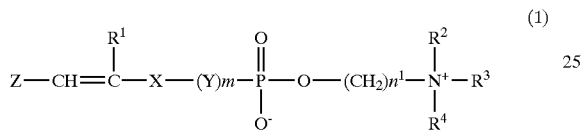

(1)

wherein X represents a divalent organic residue, Y represents an alkyleneoxy group having 1 to 6 carbon atoms, Z represents a hydrogen atom or a group R$^5$—O—CO— (wherein R$^5$ represents an alkyl group having 1 to 10 carbon atoms or a hydroxyalkyl group having 1 to 10 carbon atoms), R$^1$ represents a hydrogen atom or a methyl group, R$^2$, R$^3$ and R$^4$ are the same or different groups and each represents a hydrogen atom or a hydrocarbon or hydroxyhydrocarbon group having 1 to 6 carbon atoms, m is 0 or 1, and n$^1$ is an integer of 2 to 4;

wherein a combination of said copolymer (A2) and polymer (C) is selected from the group consisting of 2-(meth)acryloyloxyethyl-2'-(trimethylammonio)ethyl phosphate-(meth)acrylic acid copolymer and acrylic acid-butyl methacrylate copolymer; 2-(meth) acryloyloxyethyl-2'-(trimethylammonio) ethyl phosphate-(meth) acrylic acid copolymer and acrylic acid-stearyl methacrylate copolymer; 2-(meth) acryloyloxyethyl-2'-trimethylammonio) ethyl phosphate-(meth)acrylic acid copolymer and ethylene oxide-propylene oxide block copolymer; and 2-(meth) acryloyloxyethyl-2'-(trimethylammonio)ethyl phosphate-(meth) acrylic acid copolymer and vinyl pyrrolidone-styrene copolymer.

6. A hydrogel substantially soluble in water at an ordinary temperature prepared by stirring the composition for hydrogel of claim 5 in an aqueous medium to gelate the composition.

7. The hydrogel of claim 6 further comprising therein one or more members selected from the group consisting of a drug, a biopolymer other than said copolymer (A2) and said polymer (C), and a biological cell.

8. The composition of claim 5 wherein a ratio of said copolymer (A2) to said polymer (C) is 1:15 to 15:1 in weight ratio.

9. A composition for hydrogel substantially soluble in water at an ordinary temperature comprising:

a copolymer (A1) having a phosphorylcholine-like group soluble in an aqueous medium, said copolymer (A1) comprising 25 to 97 mol % of unit (a) derived from at least one compound represented by the formula (1) having a phosphorylcholine-like group, and 3 to 75 mol % of unit (b) derived from at least one of hydrophobic monomers represented by the formula (2): and a copolymer (A2) having a phosphorylcholine-like group soluble in an aqueous medium, said copolymer (A2) comprising 30 to 90 mol % of unit (a) derived from at least one compound represented by the formula (I) having a phosphorylcholine-like group, and 10 to 70 mol % of unit (c) other than said unit (a) derived from a monomer having one or more hydrophilic groups selected from the group consisting of a hydroxyl group, a carboxyl group, a phosphonic acid group, a sulfonic acid group, an amide group, an amino group, a dialkylamino group, a trialkylammonium salt group, a trialkylphosphonium salt group and a polyoxyethylene group:

$$Z-CH=\overset{R^1}{\underset{}{C}}-X-(Y)m-\overset{O}{\underset{O^-}{\overset{\|}{P}}}-O-(CH_2)n^1-\overset{R^2}{\underset{R^4}{\overset{|}{N^+}}}-R^3 \quad (1)$$

wherein X represents a divalent organic residue, Y represents an alkyleneoxy group having 1 to 6 carbon atoms, Z represents a hydrogen atom or a group R$^5$—O—CO—(wherein R$^5$ represents an alkyl group having 1 to 10 carbon atoms or a hydroxyalkyl group having 1 to 10 carbon atoms), R$^1$ represents a hydrogen atom or a methyl group, R$^2$, R$^3$ and R$^4$ are the same or different groups and each represents a hydrogen atom or a hydrocarbon or hydroxyhydrocarbon group having 1 to 6 carbon atoms, m is 0 or 1, and n$^1$ is an integer of 2 to 4:

$$CH_2=\overset{R^6}{\underset{}{C}}-L^1-L^2 \quad (2)$$

wherein R$^6$ represents a hydrogen atom or a methyl group, L$^1$ represents —C$_6$H$_4$—, —(C=O)—O—, —O—, —(C=O)NH—, —O—(C=O)— or —O—(C=O)—O— and L$^2$ represents a hydrophobic functional group selected from a hydrogen atom, —(CH$_2$)$_n^2$-L$^3$ and –((CH$_2$)p-O)L$^3$, wherein n$^2$ is an integer of 1 to 24, p is an integer of 3 to 5 and L$^3$ represents a hydrogen atom, a methyl group, —C$_6$H$_5$ or —O—C$_6$H$_5$;

wherein a combination of said copolymer (A1) and said copolymer (A2) is selected from the group consisting of 2-(meth)acryloyloxyethyl-2'-(trimethylammonio) ethyl phosphate-butyl (meth)acrylate copolymer and 2-(meth)acryloyloxyethyl-2'-(trimethylammonio) ethyl phosphate-(meth)acrylic acid copolymer; 2-(meth) acryloyloxyethyl-2'-(trimethylammonio) ethyl phosphate-lauryl (meth)acrylate copolymer and 2-(meth) acryloyloxyethyl-2'(trimethylammonio)ethyl phosphate-(meth) acrylic acid copolymer; and 2(meth) acryloyloxyethyl-2'-(trimethylammonio) ethyl phosphate-stearyl (meth)acrylate copolymer and 2-(meth) acryloyloxyethyl-2'-(trimethylammonio) ethyl phosphate-(meth)acrylic acid copolymer.

10. A hydrogel substantially soluble in water at an ordinary temperature prepared by stirring the composition for hydrogel of claim 9 in an aqueous medium to gelate the composition.

11. The hydrogel of claim 10 further comprising therein one or more members selected from the group consisting of a drug, a biopolymer other than said copolymer (A1) and said copolymer (A2), and a biological cell.

12. The composition of claim 9 wherein a ratio of said copolymer (A1) to said copolymer (A2) is 1:15 to 15:1 in weight ratio.

* * * * *